United States Patent
Tomassetti et al.

(10) Patent No.: US 11,178,851 B2
(45) Date of Patent: Nov. 23, 2021

(54) ANIMAL TRAINING AND BEHAVIOR ALTERING DEVICE AND METHOD

(71) Applicants: Peter C. Tomassetti, Pompano Beach, FL (US); Louis D. Tomassetti, Pompano Beach, FL (US)

(72) Inventors: Peter C. Tomassetti, Pompano Beach, FL (US); Louis D. Tomassetti, Pompano Beach, FL (US)

(73) Assignee: L.P.I. CONSUMER PRODUCTS, INC., Pompano Beach, FL (US)

( * ) Notice: Subject to any disclaimer, the term of this patent is extended or adjusted under 35 U.S.C. 154(b) by 288 days.

(21) Appl. No.: 16/374,158

(22) Filed: Apr. 3, 2019

(65) Prior Publication Data
US 2020/0315137 A1 Oct. 8, 2020

(51) Int. Cl.
*A01K 15/02* (2006.01)
*A61K 9/12* (2006.01)

(52) U.S. Cl.
CPC .............. *A01K 15/02* (2013.01); *A61K 9/124* (2013.01)

(58) Field of Classification Search
CPC ........ A01K 15/02; A01K 29/00; A01K 15/00; A01K 15/021; A01K 15/022; A01M 29/12; A61K 9/124; Y10S 119/905
See application file for complete search history.

(56) References Cited

U.S. PATENT DOCUMENTS

| | | | |
|---|---|---|---|
| 4,735,803 A | 4/1988 | Katz et al. | |
| 4,847,292 A | 7/1989 | Katz et al. | |
| 5,501,179 A * | 3/1996 | Cory | A01K 15/023 119/712 |
| 7,174,856 B2 | 2/2007 | Neri | |
| 7,658,166 B1 | 2/2010 | Rheinschmidt, Jr. et al. | |
| 8,037,848 B2 * | 10/2011 | Mushenski | A01K 15/02 119/719 |
| 8,051,806 B2 * | 11/2011 | Mushenski | A01K 15/021 119/719 |
| 8,904,968 B1 * | 12/2014 | Nelson | A01M 31/002 119/712 |
| 9,044,395 B2 | 6/2015 | McGlone et al. | |
| 9,247,714 B1 * | 2/2016 | Tait | A01K 15/021 |
| 9,326,491 B1 * | 5/2016 | Hegarty | A01K 29/00 |
| 9,395,161 B1 * | 7/2016 | Hegarty | A01K 15/02 |
| 9,398,756 B2 * | 7/2016 | Eckert | A01K 15/02 |
| 10,264,781 B2 * | 4/2019 | Ryan | B05B 15/68 |
| 2003/0136353 A1 * | 7/2003 | Cory | A01K 15/02 119/712 |
| 2013/0071337 A1 * | 3/2013 | McGlone | A61K 9/12 424/45 |
| 2016/0088829 A1 * | 3/2016 | Schroeder | B65D 83/752 239/172 |

* cited by examiner

*Primary Examiner* — Trinh T Nguyen
(74) *Attorney, Agent, or Firm* — Malloy & Malloy, P.L.; Robert M. Downey

(57) ABSTRACT

An animal training and behavior altering device and method is used to teach and train dogs, cats and most other animals from unwanted behaviors such as continuous barking, jumping up, stealing, pet to pet confrontations, unwanted use of furniture and other bad habits and behaviors. The device and method combines sound and smell to trigger senses of the animal in a manner that establishes and reinforces negative feedback. In particular, discharge of a propellant through a specially designed nozzle on a canister creates a loud hissing sound combined with a citrus scent that most animals strongly dislike, whereby the behavior of the animal is corrected.

16 Claims, 2 Drawing Sheets

ANIMAL TRAINING AND BEHAVIOR ALTERING DEVICE AND METHOD

BACKGROUND OF THE INVENTION

Field of the Invention

The present invention relates to a device and method for training and altering behavior of animals by combining a loud hissing noise and a scent that most animals are known to strongly dislike.

Discussion of the Related Art

Correcting undesirable animal behavior can be very challenging, particularly if the behavior has been ongoing and habitual. In the past, numerous devices and methods have been proposed by others for eliminating bad behavior of domestic animals, such as dogs and cats. In particular, devices for correcting animal behavior through negative feedback stimulation are well-known in the art. These devices include electric shock collars, ultrasonic sound emitting devices and vibrating devices. In many instances, devices of this nature inflict a significant amount of pain and/or stress to the animal and, for this reason, they are considered to be cruel and inhumane.

In an effort to provide a device that avoids pain and excessive stress to the animal, others have proposed use of a burst of pressurized gas released from a canister that is directed at the animal. These devices typically use an inert gas in a pressurized spray canister with a nozzle cap that is operated to release a burst of gas through the nozzle. The user approaches the animal while holding the spray canister in one hand, until the nozzle cap is approximately 30-50 centimeters from the animal. Then, while pointing the nozzle directly at the animal, the user operates the device, by pressing down on the top of the cap, causing a sudden release of gas in a short, fast stream that strikes the animal, usually in the face or back of the head. This creates a non-pleasant stimulus and negative feedback that the animal associates with the behavior. An example of this device is disclosed in U.S. Pat. No. 7,174,856. While this device has been found to be generally effective in modifying animal behavior, it can require repeated use to establish a negative neuro association in the animal that eventually corrects the bad behavior, and some dogs and cats simply fail to respond, in which case the undesirable behavior remains uncorrected.

Accordingly, there is a need for an improved device and method for training and altering animal behavior that avoids infliction of pain and/or undue stress to the animal and which quickly establishes a negative neuro association with the undesirable behavior, to timely correct the behavior. Moreover, there is a need for an animal training and behavior altering device that combines sound and smell to reinforce the neuro association with the undesirable behavior, thereby quickly correcting the undesirable behavior of the animal.

SUMMARY OF THE INVENTION

The present invention is directed to an animal training and behavior altering device that is particularly useful for dogs and cats, but that is also effective on other animals as well. The animal training and behavior altering device is used to teach and train animals (e.g., dogs) from unwanted behaviors such as continuous barking, jumping up, stealing, pet to pet confrontation, unwanted use of furniture and other bad habits and behaviors. The device and method works by triggering the animal's highly developed senses of sound and smell.

The device of the present invention includes a spray canister filled with a propellant, and a cap that is fitted to the top of the canister. The cap includes a specially designed nozzle and an actuator button on the top of the cap. Upon pressing down on the actuator button on the top of the cap, a burst of propellant is released through the nozzle which creates a loud hissing sound. Most animals associate a loud hissing sound to be a warning that can often be followed up with aggression if the warning is not headed. Dogs, cats and other animals in nature instinctively react to loud hissing sounds and seek refuge.

The device of the present invention combines a propellant that is infused with one or more natural citrus oils. It has been discovered that dogs, cats and other animals strongly dislike the smell of citrus. This includes citrus fruits such as oranges, lemons, limes and grapefruit.

To operate the device of the present invention, when a dog is displaying an unwanted behavior, the nozzle device is directed away from the animal and the operator and the operator presses down on the actuator button. Upon release of the propellant and infused natural citrus oil from the nozzle, the animal will experience a hissing warning sound combined with the hint of citrus smell to reinforce the directive. Using the device along with commands (repeatedly if necessary) will train and alter the animal to the desired behavior.

Objects and Advantages of the Invention

Considering the forgoing, it is a primary object of the present invention to provide an improved animal training and behavior altering device that combines sound and smell to reinforce a negative neuro association with the undesirable behavior.

It is a further object of the present invention to provide an animal training and behavior altering device that creates a loud hissing noise combined with a citrus smell that most animals strongly dislike, thereby reinforcing the neuro association with the bad behavior, and quickly correcting the bad behavior.

These and other objects and advantages of the present invention are more readily apparent with reference to the following detailed description taken in conjunction with the accompanying drawings.

BRIEF DESCRIPTION OF THE DRAWINGS

For a fuller understanding of the nature of the present invention, reference should be made to the following detailed description taken in conjunction with the accompanying drawings in which.

Like reference numerals refer to like parts throughout the several views of the drawings.

DETAILED DESCRIPTION OF THE PREFERRED EMBODIMENT

Figure 1:
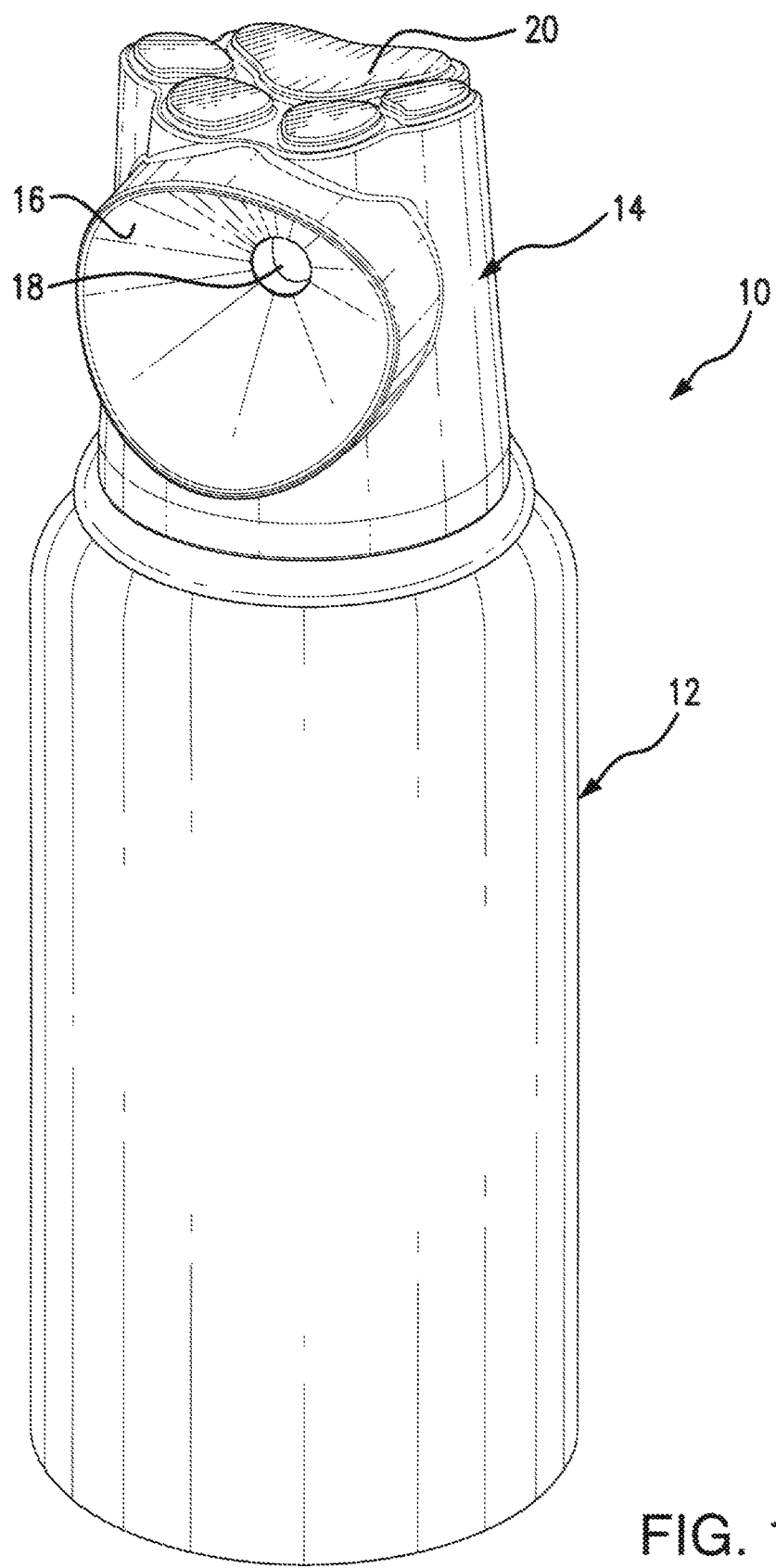
FIG. 1 is a top front perspective view of the device of the present invention including a canister and actuator cap with a spray nozzle that creates a loud hissing noise upon release of a propellant infused with a citrus scent from the canister.
Figure 2:
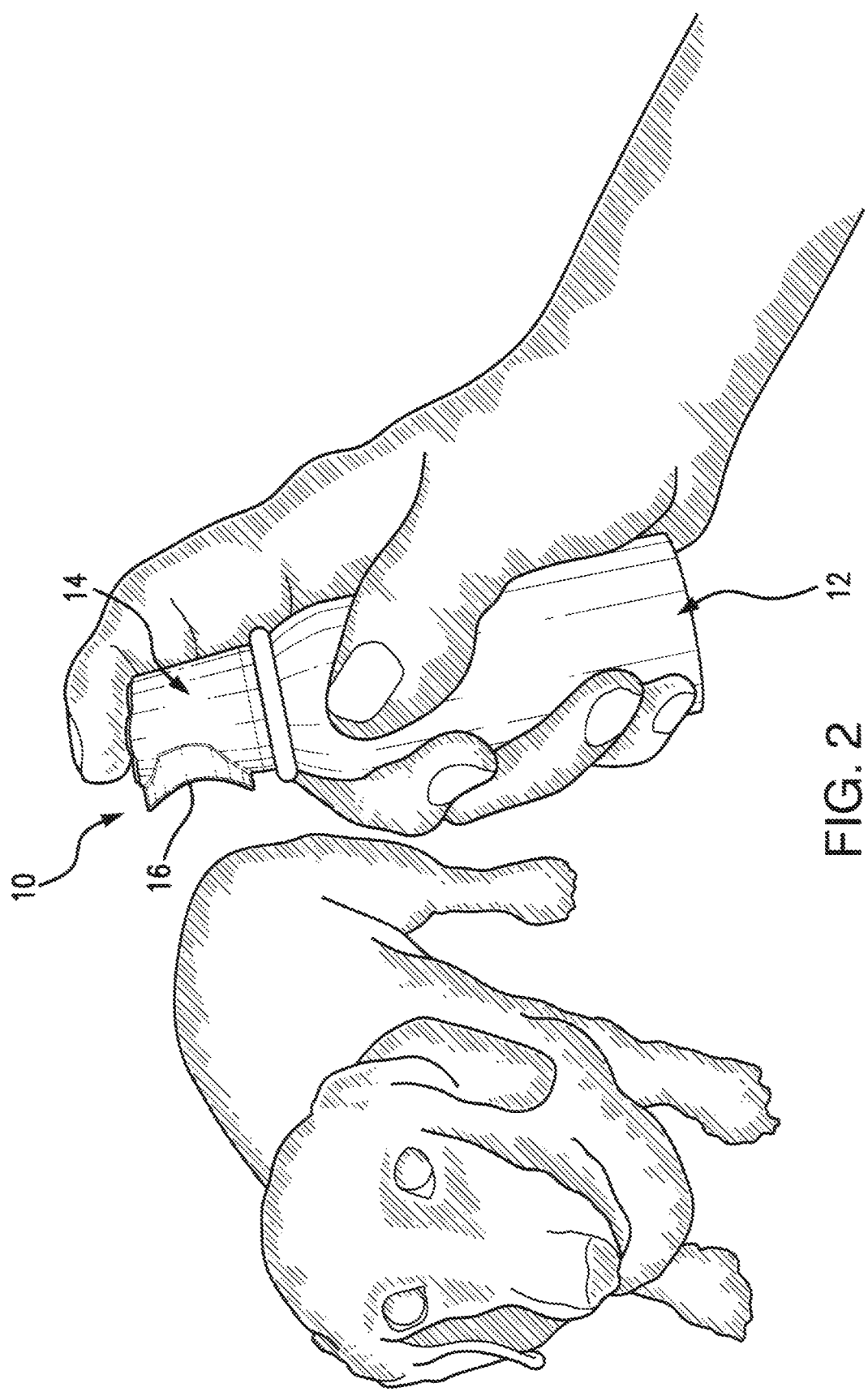
FIG. 2 is a perspective view showing use of the device of the present invention, and in accordance with the method of the present invention, to train and alter the undesirable behavior of a dog.

Referring to FIG. 1, the device of the present invention is shown and is generally indicated as 10. The device includes a canister 12 and a cap 14 fitted to a top of the canister. The cap includes a spray nozzle 16 with an aperture 18. A top of the cap 14 is formed to provide a button 20 that is intended to be pressed downwardly in order to actuate release of a propellant from the canister 12 and through the aperture 18 and out of the nozzle 16 of the cap.

Release of the propellant from the nozzle of the cap creates a loud hissing noise. More specifically, upon pressing downwardly on the button 20 of the cap 14, a burst of propellant is released from the canister and out from the aperture 18 of the nozzle 16 creating the loud hissing noise.

The propellant contained within the canister 12 is infused with one or more citrus oils so that upon release of the burst of propellant from the nozzle, a citrus scent is emitted into the surrounding atmosphere. In several embodiments of the invention, the citrus oils are natural citrus oils including: orange oil; lemon oil; lime oil; and grapefruit oil. In one embodiment, the natural citrus oil is any one of: orange oil; lemon oil; lime oil; and grapefruit oil. In another embodiment, two or more of these natural citrus oils are combined.

In use, the canister 12 is held in one hand and the button 20 is pressed downwardly on the top of the cap 14 while pointing the nozzle 16 in a direction generally away from both the user and the animal. The released burst of propellant and citrus scent is sensed by the animal to immediately create a negative neuro association with the current behavior of the animal. More specifically, when the propellant and citrus scent is released, the loud hissing sound and scent of citrus effects the animal's highly developed senses of sound and smell, creating the negative association with the animal's current behavior. This acts to quickly correct the undesirable behavior.

The propellant may be an inert gas such as 1, 1-difluoroethane, butane, propane, isobutane or a mixture of these and/or other inert gases.

While the present invention has been shown and described in accordance with a preferred and practical embodiment, it is recognized that departures from the instant disclosure are fully contemplated within the spirit and scope of the present invention which is not to be limited except as defined in the following claims.

What is claimed is:

1. A method for training an animal and altering the animal's behavior comprising the steps of:

releasing a burst of propellant infused with at least one natural citrus oil from a canister wherein the released burst of propellant is directed away from the animal and user;

directing the released burst of propellant through a nozzle on a top of the canister;

producing a loud hissing noise and citrus scent negatively impacting the animal's senses of sound and smell; and establishing and reinforcing a negative feedback in the animal associated with the behavior being corrected.

2. The method as recited in claim 1 wherein the animal is a dog.

3. The method as recited in claim 1 wherein the at least one natural citrus oil includes orange oil.

4. The method as recited in claim 1 wherein the at least one natural citrus oil includes lemon oil.

5. The method as recited in claim 1 wherein the at least one natural citrus oil includes lime oil.

6. The method as recited in claim 1 wherein the at least one natural citrus oil includes grapefruit oil.

7. The method as recited in claim 1 wherein the propellant is infused with a blend of two or more natural citrus oils.

8. The method as recited in claim 1 wherein the propellant is selected from the group consisting essentially of 1, 1-difluoroethane, butane, propane, and isobutane.

9. A method for training an animal and altering the animal's behavior comprising the steps of:

releasing a burst of propellant infused with at least one natural citrus oil from a canister;

directing the released burst of propellant through a nozzle on a top of the canister and in a direction that is away from the animal and user;

producing a loud hissing noise and citrus scent negatively impacting the animal's senses of sound and smell; and establishing and reinforcing a negative feedback in the animal associated with the behavior being corrected.

10. The method as recited in claim 9 wherein the animal is a dog.

11. The method as recited in claim 9 wherein the at least one natural citrus oil includes orange oil.

12. The method as recited in claim 9 wherein the at least one natural citrus oil includes lemon oil.

13. The method as recited in claim 9 wherein the at least one natural citrus oil includes lime oil.

14. The method as recited in claim 9 wherein the at least one natural citrus oil includes grapefruit oil.

15. The method as recited in claim 9 wherein the propellant is infused with a blend of two or more natural citrus oils.

16. The method as recited in claim 9 wherein the propellant is selected from the group consisting essentially of 1, 1-difluoroethane, butane, propane, and isobutane.

* * * * *